US006391876B1

(12) United States Patent
Dubini et al.

(10) Patent No.: US 6,391,876 B1
(45) Date of Patent: May 21, 2002

(54) REBOXETINE FOR TREATMENT OBSESSIVE COMPULSIVE DISORDERS AND PANIC DISORDER

(75) Inventors: Adriana Dubini, Milan (IT); John Michael McCall; Duncan Paul Taylor, both of Kalamazoo, MI (US); Philip F. Von Voigtlander, Plainwell, MI (US); Erik Ho Fong Wong, Portage, MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/673,768

(22) PCT Filed: Apr. 2, 1999

(86) PCT No.: PCT/US99/04288

§ 371 Date: Oct. 19, 2000

§ 102(e) Date: Oct. 19, 2000

(87) PCT Pub. No.: WO99/52518

PCT Pub. Date: Oct. 21, 1999

Related U.S. Application Data

(60) Provisional application No. 60/081,632, filed on Apr. 13, 1998, and provisional application No. 60/085,033, filed on May 11, 1998.

(30) Foreign Application Priority Data

Sep. 23, 1998 (IT) ......................... MI98A0870

(51) Int. Cl.$^7$ ............................................. A61K 31/535
(52) U.S. Cl. ................................................. 514/239.2
(58) Field of Search ...................................... 514/239.2

(56) References Cited

U.S. PATENT DOCUMENTS

| 4,229,449 A | 10/1980 | Melloni et al. | 424/248 |
| 5,068,433 A | 11/1991 | Melloni et al. | 564/349 |
| 5,391,735 A | 2/1995 | Melloni et al. | 544/174 |

FOREIGN PATENT DOCUMENTS

| DE | 29 01 032 A | 8/1979 |
| DE | 35 40 093 A | 5/1986 |
| WO | WO99/20279 | 4/1999 |

OTHER PUBLICATIONS

"Depression and Anxiety: New Tools for Diagnosis and Treatment" J. Clin. Psychiatry—W. J. Katon (vol. 59, No. Suppl. 20, 1998, pp. 3–4 XP002113302.

"Noradrenergic Versus Serotonergic Antidepressants" Predictors of Treatment Response J. Clin. Psychiatry, A.F. Schatzberg, (vol. 59, No. Suppl. 14, 1998, pp. 15–18, XP002113303.

"The Place of Reboxetine in Antidepressant Therapy" J. Clin. Psychiatry, S.A. Montgomery, vol. 59, No. Suppl. 14, 1998, pp. 26–29, XP002113304.

"Noradrenaline–selective versus serotonin–selective antidepressant therapy: differential effects on social functioning" J. Psychopharmacol, A. Dubini, et al. vol. 11, No. 4 Suppl., 1997, pp. S17–S23 XP002113305.

"Reboxetine: a review of antidepressant tolerability" J. Psychopharmacol, M. Mucci—vol. 11, No. 4 Suppl, 1997, pp. S33–S37, XP002113306.

"Efficacy and tolerability of reboxetine compared with imipramine in a double–blind study in patients suffering from major depressive episodes" H. Berzewski, et al., vol. 7, No. Suppl. 1, 1997, pp. S37–S47, XP002113307.

"Do noradrenaline and serotonin deffernetially affect social motivation and behaviour?" A. Dubini, et al., Eur. Neurophsychopharmacol., vol. 7, No. Suppl. 1, 1997, pp. S49–S55, XP002113308.

"Discussion" Eur. Neuropsychopharmacol, vol. 7, No. Suppl 1, 1997, pp. S71–S73, XP002113310 abstract.

"Does selectivity matter?" D.F.W. Deakin: Int. Clin. Psychopharmacol., vol. 11, No.: Suppl. 1, 1996, pp. 13–17, XP002113310.

B. E. Leonard, *European Neuropsychopharmacology*, 7 Suppl. 1, "Noradrenaline in Basic Models of Depression" pp. S11–S16; discussion S71–3 (1997).

J. Svestka, *Cesk–Psychiatr*, "Antidepressives of the $3^{rd}$, $4^{th}$, and $5^{th}$ Generation", 90(1): 3–19 (1994).

RE Hales, et al, *The American Psychiatric Press Textbook Psychiatry, Second Edition*, "Anxiety Disorders", (1994).

*Primary Examiner*—William R. A. Jarvis
(74) *Attorney, Agent, or Firm*—Thomas A. Wootton; Andrew M. Solomon; Stephen L. Nesbitt

(57) ABSTRACT

This invention relates to the use of reboxetine in the treatment of Obsessive Compulsive Disorders and Panic Disorders.

5 Claims, No Drawings

US 6,391,876 B1

REBOXETINE FOR TREATMENT OBSESSIVE COMPULSIVE DISORDERS AND PANIC DISORDER

This application is a 371 of PCT/US99/04288, filed Apr. 2, 1999, which claims priority to provisional application No. 60/081,632, filed Apr. 13, 1998 and No. 60/085,033, filed May 11, 1998.

FIELD OF THE INVENTION

This invention describes new treatments for several nervous system disorders, including: Obsessive Compulsive Disorders, and panic Disorder. The treatment involves the administration of the drug reboxetine.

BACKGROUND

The introduction of tricyclic antidepressants in the early 1960s has provided a major advance in the treatment of neuropsychiatric disorders. Reactive and endogenous depressions, diagnoses formerly carrying grave prognostic implications, have become, with the introduction of the tricyclic, manageable disorders with a much smaller toll on the patient and the society as a whole.

The early tricyclic compounds were reuptake inhibitors of all the catecholamines released in the synaptic cleft, thus resulting in prolongation and enhancement of the dopamine (DA), noradrenaline (NA) and serotonin (5-hydroxytryptamine=5-HT) action. Lack of selectivity also causes undesired side effects particularly on the acetylcholine (especially the muscarinic component), and histamine mediated neurotransmission.

Because of these unwanted pharmacodynamic activities, cognitive impairment, sedation, urinary and gastrointestinal tract disturbances, increased intraocular pressure were limiting factors in the clinical use of these compounds and often required discontinuation of treatment. Of utmost concern were also the cardiac toxic effects and the proconvulsant activity of this group of drugs.

More recently, selective reuptake inhibitors for serotonin (SSRI) have been introduced with definite advantages in regard to fewer side effects without loss of efficacy.

Here we present the surprising finding that one particular drug from a new category of antidepressants, a so called noradrenaline (NA) reuptake inhibitor can be used to manage or treat a few special diseases, diseases having symptoms outside of what are usually considered depression symptoms.

SUMMARY OF THE INVENTION

This patent application describes the treatment of Obsessive Compulsive Disorders (OCD), and panic Disorder (PD), comprising administering a therapeutically effective, nontoxic dose of reboxetine and derivatives and or pharmaceutically acceptable salts thereof to a patient.

Reboxetine is the generic name of the pharmaceutical substance with the chemical name of 2-(I-((2-ethoxyphenoxy)benzyl)-morpholine and its pharmaceutically acceptable salts. Reboxetine can be a free base, or it can include reboxetine methanesulfonate (also called reboxetine mesylate) or any other pharmaceutically acceptable salt that does not significantly affect the pharmaceutical activity of the substance.

A preferred dose range is 4 to 10 mg per patient per day and the most preferred dose is 6 to 8 mg or 8 to 10 mg per patient daily, depending upon the patient, delivered twice a day (b.i.d.).

ADDITIONAL DESCRIPTION OF THE INVENTION AND DESCRIPTION OF THE PREFERRED EMBODIMENT(S)

Reboxetine is the generic name of the pharmaceutical substance with the chemical name of 2-(I-((2-ethoxyphenoxy)benzyl)-morpholine, and its pharmaceutically acceptable salts. Reboxetine can be a free base, or it can include reboxetine methanesulfonate (also called reboxetine mesylate) or any other pharmaceutically acceptable salt that does not significantly affect the pharmaceutical activity of the substance. Reboxetine and a method of synthesis are described in U.S. Pat. No. 4,229,449, issued Oct. 21, 1980, Melloni et. al., incorporated by reference, methods of preparation are described in U.S. Pat. No. 5,068,433, issued Nov. 26, 1991, Melloni et. al. and in U.S. Pat. No. 5,391,735, issued Feb. 21, 1995, both incorporated by reference. Reboxetine may also be known under the trade name of EDRONAX™.

The pharmaceutical compositions and methods of administration described in U.S. Pat. No. 4,229,449 at col. 18, lines 33–66 are specifically incorporated by reference. Twice a day dosing is preferred with current formulations.

Reboxetine acts as an antidepressant. Antidepressants are frequently grouped into categories or "generations". The first generation of antidepressants were usually tricyclic antidepressants such as maprotiline that affected various neurotransmitter systems and are associated with many undesirable side effects. The second generation of antidepressants, such as mianserine, mirtrazapine and trazodone are largely devoid of anticholinergic action and their adrenolytic and antihistaminic effects are weaker. These are contrasted with the third generation of antidepressants (e.g. SSRI, ipsapirone, viloxazine, reboxetine, bupropione) that mediate only one of the three main neurotransmitter system for depression (5-HT, noradrenaline, dopamine) and they do not affect muscarine, histamine and adrenergic cerebral systems. Svestka, J. "Antidepressives of the 3rd, 4th and 5th generation,"*Cesk-Psychiatr. February* 1994; 90(1):3–19. (Czech).

Reboxetine, however, does not act like most antidepressants. Unlike tricyclic antidepressants and even selective serotonin reuptake inhibitors (SSRIs), reboxetine is ineffective in the 8-OH-DPAT hypothermia test, indicating that reboxetine is not a selective serotonin reuptake inhibitor, instead it is selective for the noradrenergic system. Thus, reboxetine is not an SSRI, rather it is considered a novel, selective, noradrenaline-reuptake inhibitor (NARI). Leonard-BE, "Noradrenaline in basic models of depression." *European-Neuropsychopharmacol. April* 1997; 7 Suppl 1: S11-6; discussion S71-3. Unlike most drugs, reboxetine is a highly selective norepinephrine uptake inhibitor, with only marginal serotonin and no dopamine uptake inhibitory activity. The compound displays only weak or no anti-cholinergic activity in different animal models and is devoid of monoamine oxidase (MAO) inhibitory activity.

Reboxetine is highly potent and fast acting. Our investigations indicate reboxetine has potent antireserpine activity and combines the inhibitory properties of classical tricyclic antidepressants on the reuptake of noradrenaline with an ability to desensitize v-adrenergic receptor function without showing any appreciable interaction with muscarinic cholinergic and I-adrenerigic receptors. Moreover, reboxetine shows less vagolytic activity than other tricyclic antidepressants.

The inventors have discovered that in addition to its unique properties, mentioned above, reboxetine has been found particularly useful for treating or enhancing the treatment of a few psychiatric symptoms or disorders, with greater efficacy and with fewer side effects, than with treatment by known drugs. Furthermore, the inventors here have discovered that reboxetine can also be used to treat, or to enhance the treatment, of a few other specific psychiatric symptoms or disorders. The new symptoms or disorders amenable to treatment with reboxetine are provided below.

The dosage used to treat all of the disorders described here is as follows. Reboxetine is well tolerated and has a wide safety range, it can be administered in a dose range of active ingredient from about 1 to over 20 mg/kg. It is more commonly provided in dosages of from 1 to 20 mg per patient per day. The compound may be administered by any suitable method including a convenient oral dosage form. A preferred method is oral dosing twice a day. The preferred dose range is 4 to 10 mg per patient per day and the most preferred dose is 6 to 8 mg or 8 to 10 mg per patient daily, depending upon the patient, delivered twice a day (b.i.d.). It can also be given at dosages of 2, 4, 6, 8, 10 or 12 mg/patient per day or fractions thereof: For example, suitable administrations could be 4 mg in the morning and 2 or 4 mg in the evening. In some patients the ideal dosing would be 3–5 mg in the morning and 3–5 mg in the evening. A skilled practitioner would be expected to determine the precise level of dosing. The idea dosing would be routinely determined by an evaluation of clinical trials and the needs of the patient.

The diseases described for treatment here are:

1. Obsessive Compulsive Disorders (OCD)

Obsessive Compulsive Disorder is a condition or state of anxiety that may be treated with reboxetine. General descriptions of OCD, may be found in many standard sources, such as, The American Psychiatric Press Textbook of psychiatry, Second Edition, Edited by Robert E. Hales, Stuart C. Yudofsky, and John A. Talbott, copyright 1994, incorporated by reference, especially the chapter on "Anxiety Disorders," incorporated by reference. Another of many texts is the Manual of psychiatric Therapeutics, Second Edition, edited by Richard I. Shader, incorporated by reference, especially Chapter 5, Obsessions and Compulsions, more particularly, Section III of that chapter, "OCD" pp. 36 et. seq., incorporated by reference.

The treatment of Obsessive Compulsive Disorders (OCD) involves the administration of reboxetine in a manner and form that provide a reduction in the symptoms of the disease. See general description above for administration of reboxetine. The following study shows the therapeutic effectiveness of using reboxetine in doses varying from 6 to 8 mg to treat OCD. This study is provided to illustrate the usefulness of using reboxetine as a treatment for OCD and the invention described herein should not be considered limited by this example.

In a trial involving 10 patients with a DSM-III-R diagnosis of Obsessive Compulsive Disorder who were all treated with reboxetine for a period of 3 to 4 weeks with the dose for the first week at 6 mg (4 mg in a.m. and 2 mg in p.m.) with the dose increasing in the second week to 8 mg (4 mg b.i.d.). At CGI last assessment, one patient was judged very much improved, 4 were judged much improved, 2 minimally improved, while 3 were unchanged. Of the patients who did respond they had a decrease of the obsessive-compulsive symptomatology, as measured by the CPRS-OC rating scale, of more than 30 and as much as 73%.

II. Panic Disorder (PD)

panic Disorder is a condition or state of anxiety that may be treated with reboxetine. General descriptions of PD, may be found in many standard sources, such as, The American psychiatric press Textbook of psychiatry, Second Edition, Edited by Robert E. Hales, Stuart C. Yudofsky, and John A. Talbott, copyright 1994, incorporated by reference, especially the chapter on "Anxiety Disorders," incorporated by reference, another of many texts is the Manual of psychiatric Therapeutics, Second Edition, edited by Richard I. Shader, incorporated by reference, especially Chapter 25, "Approaches to the Treatment of Anxiety States," incorporated by reference.

The treatment of panic Disorder involves the administration of reboxetine in a manner and form that provide a reduction in the symptoms of the disease. See general description above for administration of reboxetine.

The following study shows the therapeutic effectiveness of using reboxetine in doses varying from 6 to 8 mg to treat panic Disorder. This study is provided to illustrate the usefulness of using reboxetine as a treatment for PD and the invention described herein should not be considered limited by this example.

In a trial involving 75 patients that satisfied the DSM-III criteria for the diagnosis of panic Disorder with or without Agoraphobia (300.01, 300.21) and had at least 4 panic attacks in the month preceding their admission, in a randomized, placebo controlled parallel group, double blind design, 37 on reboxetine and 38 on placebo, the mean number of major panic attacks for patients treated with reboxetine was significantly lower than for those on placebo. Phobic symptoms, anticipatory anxiety, occupational functioning, social and family adjustment were all better at some point in time for those treated with reboxetine than for patients on placebo.

What is claimed is:

1. A method of treating or enhancing the treatment of a disorder selected from:

a) Obsessive Compulsive Disorders (OCD); and b) Panic Disorder (PD);

comprising administering a therapeutically effective, non-toxic dose of reboxetine or any of its derivatives or a pharmaceutically acceptable salt thereof to a patient in need thereof.

2. The method of claim 1 where reboxetine is used to treat or enhance the treatment of Obsessive Compulsive Disorders (OCD).

3. The method of claim 1 where reboxetine is used to treat or enhance the treatment of Panic Disorder (PD).

4. A method as in any one of claims 1–3 where the reboxetine dose range is from 4 to 10 mg per patient per day.

5. A method as in any one of claims 1–3 where the reboxetine dose range is from 6 to 8 mg per patient per day.

* * * * *